United States Patent [19]
Parker

[11] Patent Number: 5,105,006
[45] Date of Patent: Apr. 14, 1992

[54] PHOSPHONIUM SALTS

[75] Inventor: Theodore L. Parker, Walnut Creek, Calif.

[73] Assignee: The Dow Chemical Company, Midland, Mich.

[21] Appl. No.: 358,319

[22] Filed: May 25, 1989

[51] Int. Cl.$^5$ .................. C07C 303/00; C07C 307/00; B01J 31/00
[52] U.S. Cl. ......................................... 562/30; 562/45; 562/83; 562/91; 562/113; 562/125; 564/82; 502/164
[58] Field of Search ....................... 562/73, 45, 30, 83, 562/91, 113, 125; 564/82

[56] References Cited
U.S. PATENT DOCUMENTS

| | | |
|---|---|---|
| 4,197,390 | 4/1980 | Jackson . |
| 4,302,574 | 11/1981 | Doorakian et al. . |
| 4,340,761 | 7/1982 | Doorakian et al. . |
| 4,354,015 | 10/1982 | Doorakian et al. . |
| 4,438,254 | 3/1984 | Doorakian et al. . |
| 4,602,070 | 7/1986 | Cavitt et al. . |
| 4,719,268 | 1/1988 | Hefner, Jr. et al. . |
| 4,766,184 | 8/1988 | Hefner, Jr. . |
| 4,782,124 | 11/1988 | Hefner, Jr. et al. . |

Primary Examiner—Alan Siegel
Attorney, Agent, or Firm—Janet Pauline Clark

[57] ABSTRACT

The invention is a novel phosphonium salt, useful as an initiator or catalyst in the reaction of oxirane groups in an epoxy resin with aromatic carbonate and/or ester linkages in monomeric, oligomeric, or polymeric carbonates, esters, or estercarbonates.

11 Claims, 1 Drawing Sheet

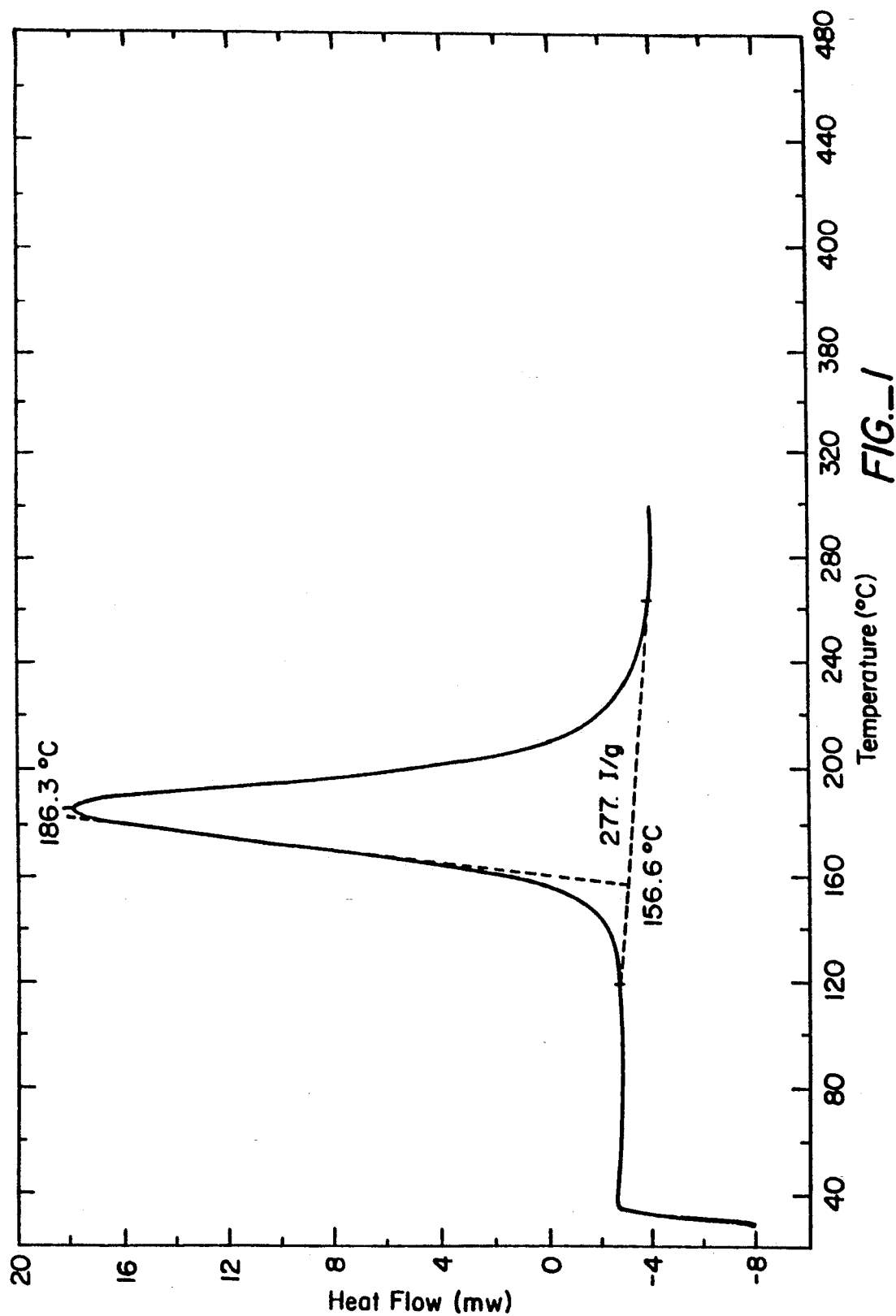

PHOSPHONIUM SALTS

BACKGROUND OF THE INVENTION

This invention relates to novel phosphonium salts. The phosphonium salts of this invention are useful as initiators/catalysts in the reaction of epoxy resins with aromatic carbonate and/or ester linkages.

Conventionally cured epoxy resins contain residual secondary hydroxyl groups derived from oxirane ring opening by active hydrogens characteristic of such cured epoxy resins. The presence of such residual hydroxyl groups in conventionally cured epoxy resins impairs the performance and properties of the cured resin by providing a site for binding of water which acts to plasticize the cured epoxy resin, thus lowering tensile and flexural strength, lowering modulus, and increasing the dielectric constant. When oxirane groups are converted by reaction with carbonate or ester groups, no alcoholic hydroxyls are generated and the reaction can therefore be utilized to make epoxy-derived thermosets which absorb less water than conventionally cured epoxies. Also, such thermosets, when prepared from carbonates, possess higher cross-link densities than conventionally cured epoxies, since each carbonate group reacts with two oxirane moieties. Consequently, the epoxy/carbonate/ester cured product possesses improved temperature performance, increased water and solvent resistance, and improved dimensional stability.

The reaction of oxirane groups with aromatic carbonate and/or ester linkages requires use of an initiator/catalyst. Known types of initiators/catalysts found to be effective for this reaction typically show activity at relatively low temperatures of about 70° to about 125° C. It has been found that in many cases, particularly when the compound containing aromatic carbonate and/or ester linkages is a polymer such as polycarbonate, polyester, or polyestercarbonate, the above mentioned initiators/catalysts do not provide a sufficient processing window for melt blending the initiator/catalyst and the epoxy resin with the compound containing carbonate and/or ester linkages.

What is needed is an active and effective initiator/catalyst for the reaction of oxirane groups in epoxy resins with aromatic carbonate and/or ester linkages whose activity begins at a temperature of about 125° C. or greater. Furthermore, the initiator/catalyst activity should be substantially developed below the decomposition temperature of the epoxy/carbonate/ester composition, which begins at about 300°-320° C. in air. The initiator/catalyst desirably does not initiate or speed up side reactions to such an extent that there does not result a cured product with a better combination of physical properties vis a vis the same epoxy resin per secured with generally comparable types of initiators/catalysts.

SUMMARY OF THE INVENTION

The invention is a novel phosphonium salt composition comprising a compound of Formula 1:

  Formula 1 wherein
R is independently in each occurrence a $C_{1-20}$ monovalent hydrocarbon radical; and
X is an anion selected from the group consisting of:
$R^1SO_3^\ominus$, $R^2COO^\ominus$, $(R_3SO_2)_2N^\ominus$, $R^1SO_2^\ominus$, $R^1OHPO_3^\ominus$, $(R^1O)_2PO_2$, and $R^1HPO_3^\ominus$,
wherein
$R_1$ is a $C_{1-12}$ monovalent hydrocarbon radical or a $C_{1-12}$ monovalent halohydrocarbon radical,
$R^2$ is a hydrogen radical, a $C_{2-12}$ monovalent hydrocarbon radical or a $C_{1-12}$ halohydrocarbon radical, and
$R^3$ is a $C_{1-12}$ monovalent hydrocarbon radical.

The novel phosphonium salts of this invention are useful as initiators/catalysts in the reactions of oxirane groups in epoxy resins containing aromatic carbonate and/or ester linkages. Such phosphonium salts generally possess activity as initiators/catalysts at temperatures above about 125° C. and their activity is substantially developed at temperatures below about 300°-320° C. The use of such phosphonium salts results in cured physical products with improved properties as compared with products obtained by use of compounds known to initiate/catalyze various adductions with oxirange.

BRIEF DESCRIPTION OF THE DRAWING

FIG. 1 illustrates a DSC curve for the combination of tetrabutylphosphonium p-toluene sulfimidate with a representative epoxy resin/polycarbonate mixture.

DETAILED DESCRIPTION OF THE INVENTION

The novel phosphonium salts of this invention are useful as initiators/catalysts in the reaction of oxirane groups in epoxy resins with aromatic carbonate and/or ester linkages. The term initiator, also sometimes referred to as a coreactive catalyst, as used herein refers to an agent used to promote the reaction wherein the agent is consumed by the reaction. The term catalyst, also sometimes referred to as a non-coreactive catalyst, as used herein refers to an agent used to promote the reaction wherein the agent is not consumed by the reaction. The phosphonium salts of this invention may act as initiators or catalysts depending upon the particular reactants.

In the preceding Formula 1, R preferably is independently in each occurrence a monovalent radical of a $C_{1-12}$ alkyl, $C_{3-12}$ cycloalkyl, $C_{6-12}$ alkylaryl, or $C_{6-12}$ aryl; more preferably a $C_{1-6}$ alkyl, $C_{6-12}$ alkylaryl, or phenyl; most preferably, ethyl, butyl, or phenyl.

X is preferably an anion selected from the group consisting of $R^1SO_3^\ominus$, $R^2COO^\ominus$, and $(R^3SO_2)_2N^\ominus$; more preferably $R^1SO_3^\ominus$ and $(R^3SO_2)_2N^\ominus$.

$R^1$ is preferably a monovalent radical of a $C_{1-12}$ alkyl, $C_{1-12}$ haloalkyl, $C_{3-12}$ cycloalkyl, $C_{3-12}$ halocycloalkyl, $C_{6-12}$ alkylaryl, $C_{6-12}$ haloalkylaryl, $C_{6-12}$ aryl, $C_{6-12}$ haloaryl; more preferably a $C_{1-6}$ alkyl, $C_{1-6}$ haloalkyl, $C_{6-12}$ alkylaryl, $C_{6-12}$ haloalkylaryl, phenyl, or halophenyl. Preferred classes of halohydrocarbyl radicals include the residues of chlorohydrocarbons; more preferably a monovalent radical of $C_{1-6}$ chloroalkyl, $C_{6-12}$ chloroalkylaryl, or chlorophenyl.

$R^2$ is preferably a monovalent radical of a $C_{2-12}$ alkyl, $C_{1-12}$ haloalkyl, $C_{3-12}$ cycloalkyl, $C_{3-12}$ halocycloalkyl, $C_{6-12}$ alkylaryl, $C_{6-12}$ haloalkylaryl, $C_{6-12}$ aryl, or $C_{6-12}$ haloaryl: more preferably a $C_{2-6}$ alkyl, $C_{1-6}$ haloalkyl, $C_{6-12}$ alkylaryl, $C_{6-12}$ haloalkylaryl, phenyl, or halophenyl. Preferred classes of halohydrocarbyl radicals include residues of chlorohydrocarbons; more preferably a monovalent radical of a $C_{1-6}$ chloroalkyl, $C_{6-12}$ chloroalkylaryl, or chlorophenyl.

$R^3$ is preferably a monovalent radical of a $C_{1-12}$ alkyl, $C_{3-12}$ cycloalkyl, $C_{6-12}$ alkylaryl, or $C_{6-12}$ aryl; more preferably a $C_{1-6}$ alkyl, $C_{6-12}$ alkylaryl, or phenyl.

As used herein, the terms halohydrocarbon, haloalkyl, halocycloalkyl, haloalkylaryl, and haloaryl refer respectively to partially or fully halo-substituted hydrocarbon, alkyl, cycloalkyl, alkylaryl, or aryl compounds or radicals.

The novel phosphonium salts of this invention may be prepared by an in situ method or a hydroxide method.

In the in situ method, a first solution is prepared by dissolving the appropriate tetraorgano-phosphonium halide, preferably chloride ($R^4P\oplus Cl\ominus$) or bromide ($R^4P\oplus Br\ominus$), in an alcohol such as methanol. The appropriate acid of the anion X in an alcohol such as methanol is added to the first solution. A second solution is prepared by dissolving an alkali metal hydroxide, such as sodium or potassium hydroxide, in an alcohol such as methanol. The two solutions are mixed to form a precipitate. Toluene may be added to the mixture. The mixture is filtered and vacuum stripped to yield the tetraorgano-phosphonium X salt, $R^4P\oplus X\ominus$, as product.

In the hydroxide method, a first solution is prepared by dissolving an alkali metal hydroxide, such as sodium or potassium hydroxide, in an alcohol such as methanol. A second solution is prepared by dissolving the appropriate tetraorgano-phosphonium halide, preferably chloride ($R^4P\oplus Cl\ominus$) or bromide ($R^4P\oplus Br\ominus$), in an alcohol such as methanol. The second solution is chilled and held at a temperature below about 10° C. while adding the first solution with agitation. A precipitate of the alkali metal halide is removed by filtration, leaving a third solution of the appropriate tetraorgano-phosphonium hydroxide, ($R^4P\oplus OH\ominus$). A fourth solution is prepared containing the appropriate acid of the anion X in an alcohol such as methanol. The third and fourth solutions are combined to give a precipitate of the appropriate tetraorgano-phosphonium X salt, ($R^4P\oplus X\ominus$) which is recovered by vacuum stripping.

The novel phosphonium salts of this invention are useful as initiators/catalysts in the reaction of oxirane groups in epoxy resins with aromatic carbonate and/or ester linkages. Suitable epoxy resins include polyglycidyl ethers, esters, and amines. Preferred epoxy resins include those represented by Formulas 2-6.

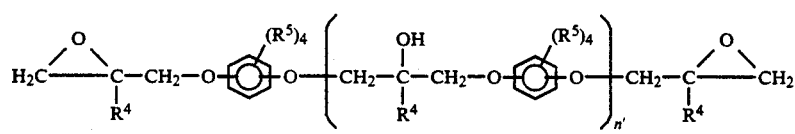

Formula 2

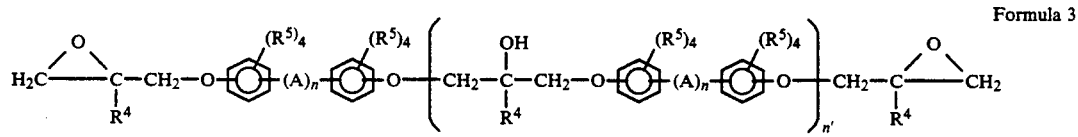

Formula 3

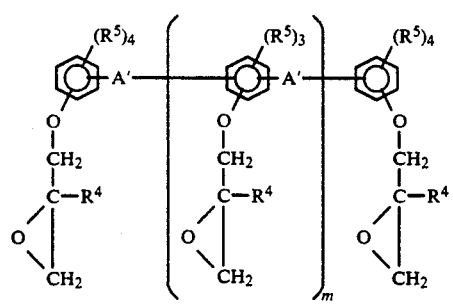

Formula 4

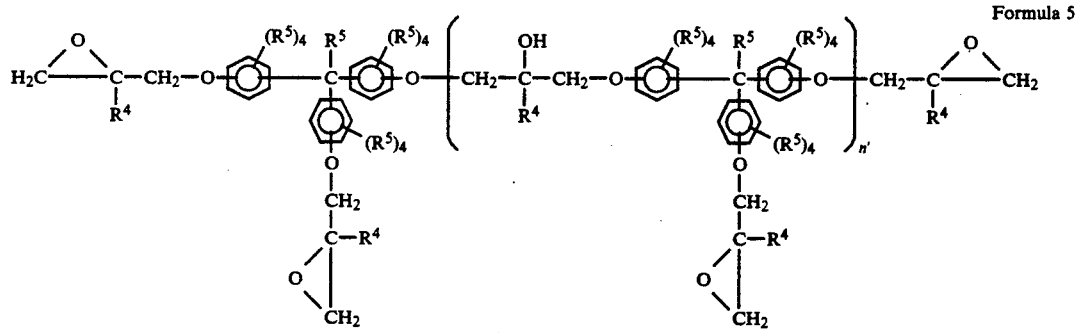

Formula 5

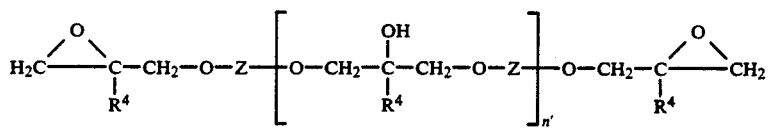

Formula 6 wherein A is a divalent hydrocarbon group having from 1 to about 12, preferably from 1 to about 6, more preferably from 1 to about 3, carbon atoms, —C(CF$_3$)$_2$—,

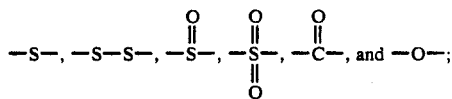

Z is a hydrocarbyl group containing from 1 to about 15 carbon atoms or a —C(R$^6$)$_2$—C(R$^6$)$_2$—[O—C(R$^6$)$_2$—C(R$^6$)$_2$]—$_{m'}$ group; A' is a divalent hydrocarbon group having from 1 to about 3, preferably 1, carbon atoms or a

group; p has a value from zero to about 10, preferably from zero to 3; each R$^4$ is independently hydrogen, a hydrocarbyl or hydrocarbyloxy group having from 1 to 18 carbon atoms or a halogen, preferably chlorine or bromine; R$^5$ is independently hydrogen or a hydrocarbyl group having from 1 to about 3 carbon atoms; each R$^6$ is independently hydrogen or a hydrocarbyl group having from 1 to about 6 carbon atoms; n has a value from zero or 1; n' has a value from zero to about 40, preferably from 0.1 to about 5; m' has a value from 1 to about 100, preferably from 1 to about 25 and m has a value from about 0.001 to about 6. Such preferred epoxy resins are more fully described in U.S. Pat. No. 4,782,124, the relevant portions of which are incorporated herein by reference for all purposes which may be legally served thereby. The epoxy resins useful in this invention preferably do not contain hydroxyl groups in amounts which cause intolerably deleterious effects on the physical properties of the cured epoxy resin/carbonate/ester products. Epoxy resins containing significant amounts of hydroxyl groups may be used by first reacting/blocking such hydroxyl groups in the epoxy resins. For example, the hydroxyl groups in such epoxy resins may be reacted with carbonates, preferably of low molecular weight, via a transesterification reaction as described in U.S. Pat. Nos. 4,766,184 and 4,782,124, the relevant portions of which are incorporated herein by reference for all purposes which may be legally served thereby.

The aromatic carbonate and/or ester compounds may be monomeric, oligomeric, or polymeric. Polymeric compounds such as polycarbonates, polyesters, and polyestercarbonates are preferred. Polycarbonates, polyesters, and polyestercarbonates derived from bisphenol A are especially preferred. Each carbonate linkage reacts with two epoxide groups; each ester linkage reacts with one epoxide group. Other than stoichiometric ratios may be used depending upon the properties desired in the pre-cured and fully cured epoxy/carbonate/ester compositions.

The epoxy resin/carbonate/ester compositions described herein generally comprise relative amounts of epoxy resins and carbonate/ester compounds such as to provide from about 1 to about 5 oxirane groups per 2 carbonate and/or ester groups. The amount of initiator/catalyst used to promote the reaction is preferably between about 0.00075 and about 1.0 millimoles (mmole) initiator/catalyst per gram of total reaction composition. Generally, the use of an initiator/catalyst based on the conjugate base of stronger acids, that is, acids with a lower pKa, results in higher temperatures, that is, secant on-set exotherm temperatures, for the initiator/catalyst. The initiators/catalysts of this invention preferably show activity above about 125° C., more preferably above about 150° C. The initiator/catalyst activity is substantially developed below the decomposition temperature of the epoxy/carbonate/ester composition, preferably below about 320° C., more preferably below about 300° C.

SPECIFIC EMBODIMENTS

The following Examples are for illustration only and are not intended to limit the scope of the invention in any manner inconsistent with the claims in this patent.

EXAMPLE 1

Preparation of Tetrabutylphosphonium Chloroacetate By In Situ Method

Tetrabutylphosphonium bromide, about 16.95 grams (0.05 mole), is dissolved in about 15.24 grams anhydrous methanol. An aliquot of this solution, about 6.44 grams (0.01 mole), is placed in a flask. Chloroacetic acid, about 0.945 grams (0.01 mole), in about 4.0 grams methanol is added to the flask. A solution containing potassium hydroxide, 89.0 weight percent, about 7.58 grams in about 18.375 grams methanol, is prepared. An aliquot of the potassium hydroxide solution, about 2.15 grams (0.01 mole), is added to the flask. A white precipitate is formed. Toluene, about 10.0 grams, is added to the mixture. The mixture is vacuum filtered through a glass frit. The filtrate is vacuum stripped at about 50° C. to yield about 3.57 grams of white solid. The product is titrated with perchloric acid in glacial acetic acid. The purity of the product is about 66.1 weight percent with the impurity being residual methanol. The yield is about 67 percent.

EXAMPLE 2

Preparation of Tetrabutylphosphonium o-Chlorobenzoate By In Situ Method

The method of Example 1 is followed using about 0.437 grams (0.01 mole) o-chlorobenzoic acid. The crystalline solid, about 1.09 grams, has a purity of about 84.7 weight percent. Yield is about 78 percent.

EXAMPLE 3

Preparation of Butyltriphenylphosphonium Chloroacetate By In Situ Method

A solution is prepared containing about 18.40 grams (0.046 mole) butyltriphenylphosphonium bromide in about 20.07 grams anhydrous methanol. An aliquot of the solution, about 8.34 grams (0.01 mole), is placed in a flask. As in Example 1, chloroacetic acid solution, followed by potassium hydroxide solution, is added to the flask. Following the work-up of Example 1, about 4.47 grams of white solid is obtained with a purity of about 65.7 weight percent. Yield is about 70 percent.

EXAMPLE 4

Preparation of Butyltriphenylphosphonium o-Chlorobenzoate By In Situ Method

The method of Example 3 is followed using about 0.437 grams o-chlorobenzoic acid. The product is an oil, about 2.72 grams, with a purity of about 69.3 weight percent. Yield is about 80 percent.

EXAMPLE 5

Preparation of Tetrabutylphosphonium p-Toluenesulfonate By Hydroxide Method

Potassium hydroxide, about 89.0 weight percent, about 7.66 grams (0.122 mole), is dissolved in about 22.85 grams anhydrous methanol. A second solution is prepared by dissolving about 20.32 grams (0.06 mole) tetrabutylphosphonium bromide in about 19.21 grams anhydrous methanol. The second solution is chilled to about 5° C. About 15.63 grams (0.06 mole) of the potassium hydroxide solution is added, keeping the temperature below about 10° C. After stirring for about 1 hour, the chilled solution is vacuum filtered to remove the precipitated potassium bromide. The concentration of tetrabutylphosphonium hydroxide in the remaining solution is determined by titration with perchloric acid in glacial acetic acid to be about 0.993 mmole/gram.

A solution is prepared containing about 1.90 grams (0.01 mole) p-toluene sulfonic acid in about 3.0 grams methanol. This solution is mixed with about 10.07 grams (0.01 mole) of the tetrabutylphosphonium hydroxide solution. The precipitate formed is recovered by vacuum stripping at about 50° C. to yield a light brown solid, about 4.56 grams, of about 90 weight percent purity.

EXAMPLE 6

Preparation of Tetrabutylphosphonium Benzene Sulfinate By Hydroxide Method

The method of Example 5 is followed. A solution is prepared containing about 2.44 grams (0.01 mole) benzene sulfinic acid in about 3.0 grams methanol. The solution is mixed with about 10.07 grams (0.01 mole) tetrabutylphosphonium hydroxide solution. After the work-up described in Example 5, about 4.19 grams of a dark brown solid is obtained.

EXAMPLE 7

Preparation of Tetrabutylphosphonium p-Toluenesulfimidate By Hydroxide Method The method of Example 5 is followed. A solution containing about 3.25 grams (0.01 mole) bis(p-tolyl)sulfimide in about 4.0 grams 50 weight percent methanol/50 weight percent tetrahydrofuran is mixed with about 10.07 grams (0.01 mole) of the tetrabutylphosphonium hydroxide solution. After the work-up described in Example 5, about 6.32 grams of a white solid of purity about 87.7 weight percent is obtained. The yield is about 95.1 percent.

The compounds of Examples 1-7 are evaluated for catalytic activity by Differential Scanning Calorimetry (DSC) with a duPont 1090 Thermal Analyzer scanning at a rate of about 10° C./minute for about 0.0157 mmole/gram initiator/catalyst and a sample size of about 10 to 30 milligrams. A sample of the catalyst/initiator whose activity is to be characterized is dissolved in an appropriate solvent, preferably methylene chloride or methanol, in an amount to give a solution with a catalyst/initiator concentration of about 0.157 mmole/g. A stock evaluation solution is prepared by mixing epoxy resin DER-332 (diglycidyl ether of bisphenol A), about 57.5 g, polycarbonate resin, about 42.5 g, and methylene chloride, about 400 g. To a 10.0 g aliquot of the stock evaluation solution is added about 200 mg of catalyst/initiator solution, which results in a catalyst/initiator concentration of about 0.0157 mmole/g based on solids content. A glass slide is cleaned with methylene chloride and dried. A few milliliters of the catalyzed test solution is placed on a slide and the solvent allowed to evaporate. Residual solvent is removed from the resultant film by heating at about 50° C. for about 30 minutes. The sample is scraped off the slide and a 10–30 mg portion placed in an aluminum SDC pan and sealed. An example of a DSC curve is illustrated by FIG. 1 for tetrabutylphosphonium p-toluene sulfimidate. Temperature is shown on the x-axis and heat flow is shown on the y-axis. A peak indicates that an exothermic transition, in this case a chemical reaction, is taking place beginning at the temperature where the heat flow deviates from the baseline. The area under the peak is related to the total heat evolved and thus the heat of reaction and the effectiveness of the catalyst. A secant line is drawn to the initial portion of the exothermic peak and extended to where it intersects the interpolated baseline. This defines the "secant onset temperature", which is the most reproducible comparative temperature reflecting where the reaction is beginning. This value represents an upper processing temperature to ensure minimal reaction during blending and processing. For a further description of the DSC test method. See *DuPont 1090 Thermal Analyzer Operator's Manual*, DuPont, Analytical Instruments Division, Concord - McKean Building, Wilmington, Del. 19898, May 1982, the relevant portions incorporated herein by reference for all legal purposes served thereby. Results are reported in Table I.

TABLE I

| PHOSPHONIUM SALTS | | | | | |
|---|---|---|---|---|---|
| | | | Exotherm | | |
| Example | Cation | Anion | Secant on-set (°C.) | Peak (°C.) | ΔHo (joules/gram) |
| 1 | tetrabutyl phosphonium | chloroacetate | 128 | 166 | 316 |
| 2 | tetrabutyl phosphonium | o-chlorobenzoate | 134 | 174 | 319 |
| 3 | butyltriphenyl phosphonium | chloroacetate | 126 | 162 | 324 |
| 4 | butyltriphenyl phosphonium | o-chlorobenzoate | 129 | 164 | 310 |
| 5 | tetrabutyl phosphonium | p-toluene sulfonate | 161 | 198 | 183 |
| 6 | tetrabutyl phosphonium | benzene sulfinate | 160 | 197 | 195 |
| 7 | tetrabutyl phosphonium | p-toluene sulfimidate | 157 | 186 | 277 |

The initiator/catalytic activity of the compounds described in Examples 1-7 begins at a temperature of greater than about 125° C., as measured by the secant on-set exotherm temperature. The peak exotherm temperatures indicate the initiator/catalytic activity of the compounds described in Examples 1-7 is substantially complete at temperatures below about 200° C.

The impure compounds synthesized in Examples 1-7 demonstrate different catalyst/initiator activity depending upon their compositions when evaluated by the standard DSC test method hereindescribed. All compounds as synthesized exhibit activity above 125° C. and therefore have not been isolated as pure compounds. However, the pure compounds can be isolated by standard recrystallization techniques such as the following.

A sample of the impure compound is dissolved in a minimum volume of a hot alcohol such as ethane near its boiling point. A small amount of hot water is optionally added until a faint "clouding" is observed. The hot mixture is filtered, then allowed to cool slowly to room temperature and finally chilled in a refrigerator. The crystals of purified product are collected by filtration, then washed with a small volume of cold ethane/water, then dried in a vacuum oven at ambient temperature overnight.

EXAMPLE 8

Initiator/Catalyst Use in Oxirane/Carbonate Reactions

A solution is prepared by dissolving bisphenol A polycarbonate, about 4.25 g (3.94 mmole/g carbonate linkages, 16.745 mmoles carbonate linkages) and about 5.75 g epoxy resin DER-332 (diglycidyl ether of bisphenol A, DGEBA) 5.75 mmole/g epoxy groups, 33.0625 mmoles epoxy groups, 1:1 stoichiometry based on two epoxide groups reacting with each carbonate linkage) in about 40.0 g methylene chloride. A second solution is prepared by dissolving tetrabutylphosphonium chloroacetate, about 0.1283 g, in about 1.40 g methylene chloride. To a 10.0 g aliquot of the first solution is added about 200 mg of the second solution, which gives an initiator concentration of about 0.0157 mmole/g on a solids basis. This combined epoxy resin/polycarbonate/initiator solution is cast onto a glass plate and the solvent allowed to evaporate over a period of about 60 minutes. The minutes to remove solvent, then cured at about 180° C. for about 2 hours followed by about 200° C. for 4 hours. The cured film coating is clear, hard, and insoluble in methylene chloride.

EXAMPLE 9

Initiator/Catalyst Use in Oxirane/Ester Reactions

A solution is prepared by dissolving an aromatic copolyestercarbonate (prepared from bisphenol A, phosgene, and tere- and iso-phthaloyl chlorides such that the mole ratio of ester to carbonate linkages is 3/1 and the ratio of terephthaloyl to isophthaloyl residues is 4/1) which has an epoxy reactive equivalent weight of 81.13 based on one epoxy group reacting with each ester linkage and two epoxy groups reacting with each carbonate linkage, about 4.92 g, and about 5.08 g epoxy resin Tactix 742 (polyglycidyl ether of a tris (hydroxyphenyl)methane-based polyphenolic novolac resin), having an epoxide equivalent weight (EEW) of 160 (6.25 mmole/g epoxy groups, 1:1 stoichiometry based on two epoxide groups reacting with each carbonate linkage and one with each ester) in about 40.0 g methylene chloride. A second solution is prepared by dissolving tetrabutylphosphonium o-chlorobenzoate, about 0.1194 g, in about 1.43 g methylene chloride containing 5 drops methanol. To a 10.0 g aliquot of the first solution is added about 200 mg of the second solution, which gives an initiator concentration of about 0.0157 mmole/g on a solids basis. This combined epoxy resin/polyestercarbonate/initiator solution is cast onto a glass plate and the solvent allowed to evaporate over a period of about 60 minutes. The resultant film was heated at about 50° C. for about 30 minutes to remove solvent, then cured at about 180° C. for about 2 hours, followed by about 200° C. for about 4 hours. The cured film coating is clear, hard, and insoluble in methylene chloride. The number ratio in this Example of oxirane to carbonate groups is 4:2 and of oxirane to ester groups is 2:2.

What is claimed is:

1. A novel phosphonium salt which exhibits activity as a catalyst/initiator, consisting essentially of a compound of the formula:

wherein

R is independently in each occurrence a $C_{1-20}$ monovalent hydrocarbon radical; and X is an anion selected from the group consisting of: $R^1SO_3\ominus$, $(R^3SO_2)_2N\ominus$, and $R^1SO_2\ominus$, wherein $R^1$ is a $C_{1-12}$ monovalent hydrocarbon radical or a $C_{1-12}$ monovalent halohydrocarbon radical, $R^3$ is a $C_{1-12}$ monovalent hydrocarbon radical.

2. The novel phosphonium salt of claim 1 wherein $R^1$ is a monovalent radical of a $C_{1-12}$ alkyl, $C_{1-12}$ haloalkyl, $C_{3-12}$ cycloalkyl, $C_{3-12}$ halocycloalkyl, $C_{6-12}$ alkylaryl, $C_{6-12}$ haloalkylaryl, $C_{6-12}$ aryl, or $C_{6-12}$ haloaryl, $R^3$ is a monovalent radical of a $C_{1-12}$ alkyl, $C_{3-12}$ cycloalkyl, $C_{6-12}$ alkylaryl, or $C_{6-12}$ aryl.

3. The novel phosphonium salt of claim 2 wherein $R^1$ is a monovalent radical of a $C_{1-6}$ alkyl, $C_{1-6}$ haloalkyl, $C_{6-12}$ alkylaryl, $C_{6-12}$ haloalkylaryl, phenyl, or halophenyl, $R^3$ is a monovalent radical of a $C_{1-6}$ alkyl, $C_{6-12}$ alkylaryl, or phenyl.

4. The novel phosphonium salt of claim 3 wherein $R^1$ is a monovalent radical of a $C_{1-6}$ chloroalkyl, $C_{6-12}$ chloroalkylaryl, or chlorophenyl.

5. A novel phosphonium salt which exhibits activity as a catalyst/initiator, consisting essentially of a compound of the formula:

wherein

R is independently in each occurrence a $C_{1-20}$ monovalent hydrocarbon radical; and X is an anion selected from the group consisting of $R^1SO_3\ominus$ and $(R^3SO_2)_2N\ominus$, wherein $R^1$ is a monovalent radical of a $C_{1-6}$ alkyl, $C_{1-6}$ haloalkyl, $C_{6-12}$ alkylaryl, $C_{6-12}$ haloalkylaryl, phenyl, or halophenyl, and $R^3$ is a monovalent radical of a $C_{1-6}$ alkyl, $C_{6-12}$ alkylaryl, or phenyl.

6. The novel phosphonium salt of claim 5 wherein said ion is

7. The novel phosphonium salt of claim 3 wherein

R is independently in each occurrence a monovalent radical of a $C_{1-12}$ alkyl, $C_{3-12}$ cycloalkyl, $C_{6-20}$ alkylaryl, or $C_{6-12}$ aryl.

8. The novel phosphonium salt of claim 7 wherein

R is independently in each occurrence a monovalent radical of $C_{1-6}$ alkyl, $C_{6-12}$ alkylaryl, or phenyl.

9. The novel phosphonium salt of claim 8 wherein R is independently in each occurrence ethyl, butyl, or phenyl radical.

10. The novel phosphonium salt of claim 9 wherein the onset of said activity begins at a temperature of above about 125° C.

11. The novel phosphonium salt of claim 10 wherein said activity is substantially developed at a temperature below about 320° C.

* * * * *